United States Patent [19]
Bashkin et al.

[11] Patent Number: 5,534,123
[45] Date of Patent: Jul. 9, 1996

[54] DENATURING SEPARATION MATRIX HAVING HYDROXYETHYL CELLULOSE FOR NUCLEIC ACID ELECTROPHORESIS

[75] Inventors: John S. Bashkin, Mountain View; David L. Barker, Foster City; Richard F. Johnston, Murphys, all of Calif.

[73] Assignee: Molecular Dynamics, Sunnyvale, Calif.

[21] Appl. No.: 500,097

[22] Filed: Jul. 10, 1995

[51] Int. Cl.$^6$ ............................. G01N 27/26; B01D 57/02
[52] U.S. Cl. .......................... 204/455; 204/451; 204/450; 204/469; 204/601; 204/605
[58] Field of Search ............................ 204/299 R, 180.1, 204/182.8, 451, 450, 469, 601, 605; 106/169

[56] References Cited

U.S. PATENT DOCUMENTS

| | | | |
|---|---|---|---|
| 4,810,183 | 3/1989 | Place et al. | 425/434 |
| 5,008,196 | 4/1991 | Connolly et al. | 435/240.2 |
| 5,089,111 | 2/1992 | Zhu et al. | 204/180.1 |
| 5,110,424 | 5/1992 | Chin | 204/180.1 |
| 5,126,021 | 6/1992 | Grossman | 204/180.1 |
| 5,164,055 | 11/1992 | Dubrow | 204/180.1 |
| 5,332,481 | 7/1994 | Guttman | 204/182.8 |
| 5,374,527 | 12/1994 | Grossman | 435/6 |

FOREIGN PATENT DOCUMENTS

| | | |
|---|---|---|
| 9111709 | 8/1991 | WIPO . |
| 9403643 | 2/1994 | WIPO . |

OTHER PUBLICATIONS

Partial Table of Contents (pp. XVI–XVII), Ion Exchangers in Analytical Chemistry, Olof Samuelson, John Wiley & Sons, 1953 Nishigaki et al., J. Biochem. 111, 144–150 (1992).

Nathakarnki & Kool et al., Electrophoresis, 1992, 13, 18–31.

Barron, Annelise E. et al., "Capillary electrophoresis of DNA in uncross–linked polymer solutions," Journal of Chromatography A, 652 (1993), pp. 3–16.

Clark, Steven M. et al., "High–Speed, Parallel Separation of DNA Restriction Fragments Using Capillary Array Electrophoresis," Bioanalytical Biochemistry, 215 (1993), pp. 163–170.

Grossman, Paul D. et al., "Capillary electrophoresis of DNA in entangled polymer solutions," Journal of Chromatography, 559 (1991), pp. 257–266.

Grossman, Paul D., "Electrophoretic separation of DNA sequencing extension products using low–viscosity entangled polymer networks," Journal of Chromatography A, 663 (1994), pp. 219–227.

Heller, Christoph et al., "Brief Report: Electrophoretic separation of oligonucleotides in replenishable polyacrylamide–filled capillaries," Applied and Theoretical Electrophoresis, 4 (1994), pp. 39–41.

Hjertén, Stellan, "High–Performance Electrophoresis Elimination of Electroendosmosis and Solute Adsorption", Journal of Chromatography, 347 (1985), pp. 191–198.

Huang, Xiaohua C. et al., "DNA Sequencing Using Capillary Array Electrophoresis," Anal. Chem., 64 (1992), pp. 2149–2154.

(List continued on next page.)

Primary Examiner—John Niebling
Assistant Examiner—Alex Noguerola
Attorney, Agent, or Firm—Schneck & McHugh

[57] ABSTRACT

A capillary electrophoresis separation matrix for single-stranded nucleic acids, along with methods for using and preparing the matrix, are disclosed. The separation matrix provides denaturing conditions and contains hydroxyethyl cellulose (HEC) in combination with urea, and preferably also includes formamide. The separation matrix may be used for DNA sizing and sequencing applications and provides a single-base resolution to approximately 500 base pairs. The separation matrix is inexpensive, easy to prepare, requires no polymerization steps, and is of low enough viscosity to be pumped easily into and out of capillary tubes for electrophoresis. The low viscosity allows for high throughput of samples and reuse of the capillary tubes for numerous separations.

20 Claims, 2 Drawing Sheets

OTHER PUBLICATIONS

Kleemiss, Maria H. et al., "Capillary electrophoresis of DNA restriction fragments with solutions of entangled polymers," *Electrophoresis,* 14 (1993), pp. 515–522.

Mathies, Richard A. et al., "Capillary array electrophoresis: an approach to high-speed, high—throughput DNA sequencing," *Nature,* vol. 359, Sep. 10, 1992, pp. 167–169.

Rochleau, Marie J. et al., "Formamide modified polyacrylamide gels for DNA sequencing by capillary gel electrophoresis," *Electrophoresis,* 13 (1992), pp. 484–486.

Ruiz–Martinez, Marie C. et al., "DNA Sequencing by Capillary Electrophoresis with Replaceable Linear Polyacrylamide and Laser–Induced Fluoresence Detection," *Anal. Chem.,* 65 (1993), pp. 2851–2858.

Singhal, Ram P. et al., "Separation of DNA restriction fragments by polymer–solution capillary zone electrophoresis; influence of polymer concentration and ion–pairing reagents," *Journal of Chromatograpy A,* 652 (1993), pp. 47–56.

DENATURING SEPARATION MATRIX HAVING HYDROXYETHYL CELLULOSE FOR NUCLEIC ACID ELECTROPHORESIS

DESCRIPTION

1. Technical Field

The present invention relates to separation matrices for capillary electrophoresis, and more particularly to separation matrices which may be used for DNA sequencing.

2. Background Art

Capillary electrophoresis (CE) is a powerful tool for rapid high resolution separations of nucleic acids. CE has been used for separation of both double-stranded DNA, as in some restriction fragment applications, and single-stranded DNA, as in DNA sequencing and other fragment sizing applications.

Most CE analysis of DNA is carried out with polyacrylamide as the main component of the support or matrix within which the samples are separated. Polyacrylamide is well-suited to CE nucleic acid fragment separations because of its high resolution capabilities. For example, see U.S. Pat. No. 5,374,527 and 5,126,021 to Grossman and U.S. Pat. No. 5,164,055 to Dubrow. As suggested in the Grossman '527 patent, however, rapid loading and reloading of materials into a capillary tube represents a significant aim in the improvement of CE. This is difficult to achieve with most forms of polyacrylamide due to their high viscosity. Currently, capillary tubes are generally discarded after a CE run in polyacrylamide.

Other difficulties with the use of polyacrylamide include the time and careful control required for polymerization and generation of appropriate polymer molecular weight distributions. In addition, air bubbles that may form within the narrow-bored capillary tubes during the acrylamide polymerization process may interfere with the separation of samples.

CE equipment, and particularly automated CE equipment, would benefit greatly from a separation matrix that may quickly and easily be prepared and introduced into the capillary tube and provide high resolution of the nucleic acid samples. It would also be advantageous to have a separation matrix which can easily be removed from the capillary tube, thus allowing a capillary tube to be reused many times by the addition of a new separation matrix for each electrophoretic run, and which avoids the use of acrylamide, a known neurological toxin.

DISCLOSURE OF THE INVENTION

The above objects have been achieved with a denaturing separation matrix for electrophoresis of nucleic acid molecules, and methods for making and using the separation matrix to achieve rapid, high resolution separations. The separation matrix contains hydroxyethyl cellulose (HEC) in combination with urea. Additionally, the separation matrix may comprise formamide.

The HEC is present in a concentration of 1 to 3% w/v, but preferably 2% w/v, of the separation matrix. The urea is present in a concentration of 5 to 7M, but preferably 6M. The formamide, when present, is in a range of less than or equal to 30% v/v of the separation matrix, but is preferably present in a concentration of 10% v/v. The HEC, urea, and formamide are prepared in an aqueous solution, preferably 1 x TBE.

The separation matrix of the present invention is appropriate for nucleic acid sequencing and fragment sizing applications in CE, or other applications requiring separations of nucleic acids in single-stranded form. The HEC and urea matrix provides denaturing conditions, necessary for sequencing applications, and allows for nucleic acid separations with high resolution. A Length-of-Read (LOR) of approximately 500 or more base pairs is equivalent to the LOR achieved with polyacrylamide matrices. The LOR is the point at which the peak spacing equals the peak width in a plot of peak spacing and peak width as a function of base number. Preparation of the separation matrix is preferably achieved by initially subjecting an aqueous solution of HEC to an ion-exchange resin to remove charged impurities. This step contributes to the high resolution achieved with the separation matrix. The formamide also serves as a denaturant, helping to reduce compressions within the nucleic acid strands, and to reduce the viscosity of the separation matrix. The relatively low viscosity of the separation matrix contributes to the ease with which it may be manipulated in CE applications.

The separation matrix is easy to prepare with commercially available, non-toxic HEC. It requires no polymerization and is of sufficiently low viscosity to be easily introduced and removed from capillary electrophoresis tubes. The separation matrix of the present invention is especially well-suited to capillary array electrophoresis. Replaceable gel matrices are beneficial for many DNA applications because they are cost-effective and allow for a high throughput of samples.

ACE separation matrix incorporating HEC as a base material and providing denaturing conditions, especially for high resolution sequencing of DNA fragments, was previously not believed to be workable, because of the relatively simple nature of the HEC molecule as compared with the complex entanglement network formed by polyacrylamide. The present invention thus represents an important advance in the fields of CE and DNA sequencing.

BEST MODE FOR CARRYING OUT THE INVENTION

Figure 1:
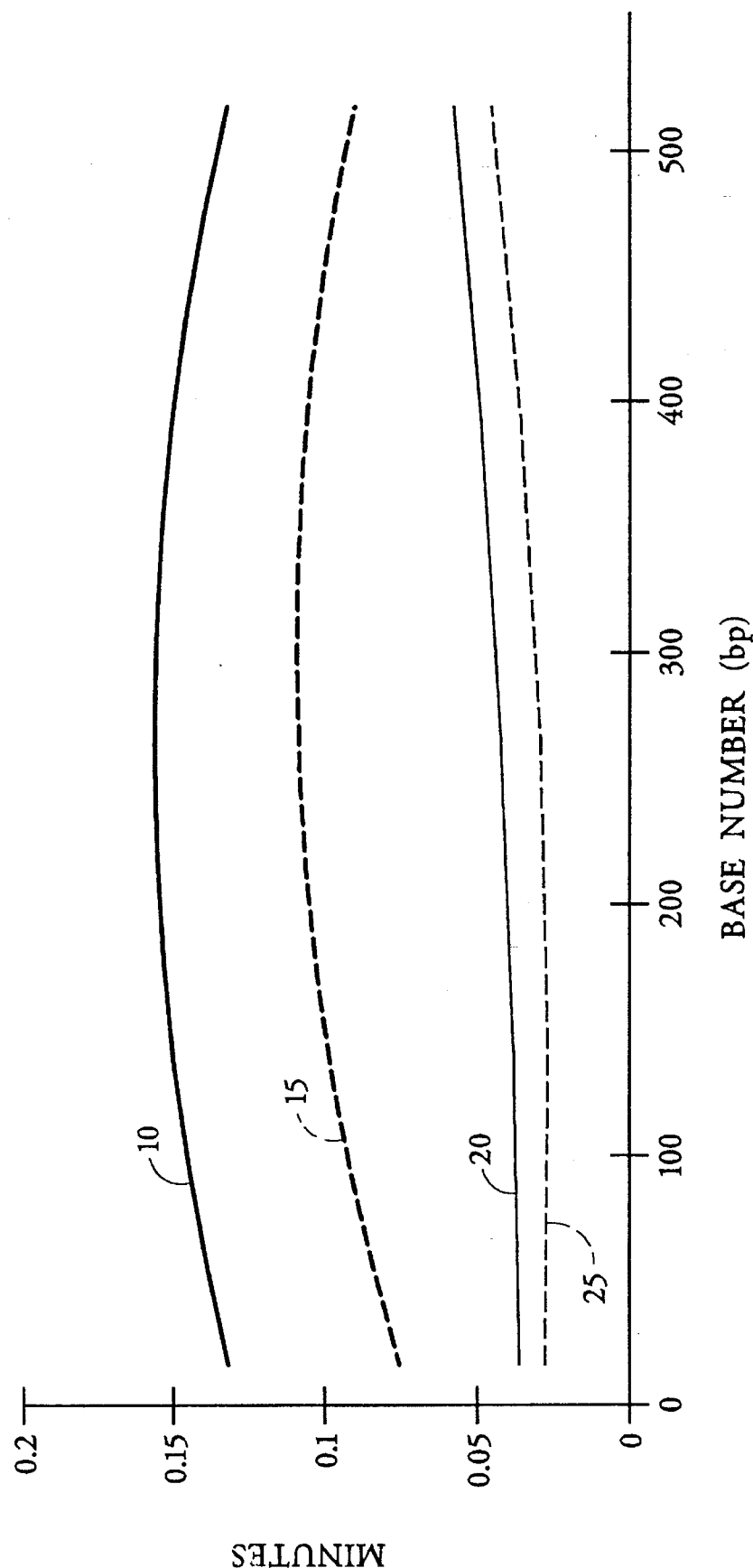
FIG. 1 is a graphical representation of peak spacings and peak widths versus base number for the separation matrix of the present invention and a prior art matrix.

The preferred embodiment of the separation matrix of the present invention contains 2% w/v HEC, 6M urea, and 10% v/v formamide in a solution of 1 x TBE. The HEC may be present in a concentration of 1–3% w/v, but 2% is optimum. The urea may be present in a concentration of 5–7M, but 6M is preferred. The formamide, when it is present in the separation matrix, is in a concentration of less than or equal to 30% v/v, but is preferably present in a concentration of 10% v/v. A 1 x TBE solution preferably serves as the aqueous solution in which the HEC and urea are dissolved, and the formamide is dispersed. 1 x TBE, or Tris-boric acid EDTA, is a well-known buffer in the field of molecular biology. It is used in experiments involving nulceic acids and generally comprises 89–90 mM Tris, 89–90 mM boric acid, and 2–5 mM EDTA (ethylenediamine tetraacetic acid) at pH 8.0–8.3. The 1 x TBE used by the present inventors comprised 89 mM Tris, 89 mM boric acid, and 2 mM EDTA at a pH of 8.0. Other buffers, such as TBE ranging in concentration from 0.5 x–2 x, or TE, or TAE, may also be used, but may require optimization of pH and other run conditions for electrophoresis.

Since oxidized forms of cellulose or other charged impurities may affect electrophoresis, the HEC is preferably purified by treatment with an ion-exchange resin which leaves the HEC substantially free of charged impurities. The HEC from different sources may vary in purity, porosity, and molecular weight, so different purification schemes may be necessary. The preferred HEC of the present invention was obtained from Polysciences in Warrington, Pennsylvania and has a molecular weight of 90,000–105,000 daltons.

The separation matrix of the present invention is typically prepared by first creating a solution of HEC and urea and purifying this solution. The first step is dissolving HEC and urea in water to produce a concentration of greater than 2% w/v of HEC and a concentration of greater than 6M of the urea. If concentrations of these two components are desired at the high end of their respective concentration ranges, then it is understood to adjust the concentrations of this first solution, for example to produce a first solution having a greater than 3% w/v concentration of HEC and a concentration of greater than 7M of urea. The HEC/urea solution is typically purified by contact with an ion-exchange resin. The ion-exchange resin should be a mixed bed strong ion-exchanger having both acidic and basic gel types. Amberlite MB-1 ion-exchange resin, available from Mallinkrodt of Paris, Ky., was used by the present inventors. Thus, a 50 ml batch of this first solution was prepared by dissolving 1.25 g HEC and 22.5 g urea in water. This solution was stirred overnight with 0.5 g Amberlite.

After purification of the HEC/urea solution by contact with the ion-exchange resin, the resin and the solution are separated, as by centrifugation. Typically, 30 minutes in a standard table-top centrifuge is sufficient. The supernatant that results comprises the purified HEC/urea solution. This supernatant is removed from the pelleted resin.

Tris, boric acid, and EDTA, preferably in the form of concentrated TBE, and, if desired, formamide are added to a portion of the purified HEC/urea solution and the solution is diluted, if necessary, to produce a separation matrix having a final concentration of 2% w/v HEC, 6M urea, 1 x TBE, and 10% v/v formamide. It is understood that adjustments to the portions and dilutions may be made to produce a separation matrix having components with other concentrations within the ranges specified.

When formamide is desired in the separation matrix, it may be added to the purified HEC/urea solution, as described above, or it may be incorporated into the original solution of HEC and urea, before the solution is purified by contact with the ion-exchange resin. If it is added to the solution prior to the purification step, then it may be necessary to create a greater than desired concentration, so that the final concentration of the formamide, after any necessary dilutions in the preparation of the separation matrix, is the desired concentration. For example, a concentration of at least 10% v/v formamide in the pre-purified solution of HEC and urea will enable preparation of a final separation matrix with a concentration of 10% v/v formamide. Formamide is useful in untangling compressions in the nucleic acid strands, which occur in areas of high guanine-cytosine nucleotide concentrations, and which may cause anomalous electrophoretic runs if left untreated. Formamide also contributes to the low viscosity of the separation matrix.

The separation matrix is then stirred for approximately 30 minutes followed by degassing under vacuum for approximately one hour. For further removal of air bubbles and impurities, the separation matrix may be centrifuged, as in microcentrifuge tubes, for 10 minutes at approximately 14,000 rpm. The resulting supernatant may then be used for filling of capillary tubes and subsequent electrophoresis. Removal of air and impurities from the separation matrix is critical in the narrow-bore context of CE applications.

The separation matrix may also be made in some other manner. For example, a 2% w/v solution of HEC and 6 or 7M solution of urea may be created directly in 1 x TBE buffer at pH 8.0. HEC and urea are dissolved overnight in the 1 x TBE, and the solution may be filtered for purification. Degassing and centrifugation of the solution, as before, may be performed before introduction of the matrix into the capillary tube for electrophoresis. Considerations such as the difficulty of preparing high concentrations of urea solutions and the relative viscosity of HEC in solution should be taken into account, however, if an alternate method is used for preparation of the separation matrix.

Once the separation matrix is prepared, a portion of it is introduced into a capillary tube, as with pressure of 400 psi. The filling process is typically completed in less than two minutes. The separation matrix of the present invention is used for CE as both the gel matrix and the run buffer for each electrode. After the filling process is complete, a pre-run is usually done for about 10 minutes at 12 kV, prior to introduction of the sample. This pre-run serves to stabilize the current. The sample is introduced at an entrance end of the capillary tube, e.g. by electrokinetic injection, and the well-known separation process of electrophoresis is performed.

It is advantageous in the CE of nucleic acids to treat the inside wall of the capillary tube with a layer of polyacrylamide, as taught by Stellan Hjertén, in "High-Performance Electrophoresis Elimination of Electroendosmosis and Solute Adsorption," *Journal of Chromatography*, 347 (1985), pages 191–198. In the method of using the separation matrix of the present invention, it is therefore preferred that the inside wall of the capillary tube be coated with polyacrylamide prior to filling of the tube with a portion of the prepared separation matrix, for best performance.

In the prior art, the use of high viscosity polyacrylamide generally required that the capillary tube and the matrix be discarded after the separation had occurred and data collected. The present invention represents an improvement, however, because the separation matrix is of sufficiently low viscosity to be easily and cleanly removed from the capillary tube.

Generally, after completion of an electrophoretic run, water is run through the capillary tube under nitrogen pressure at 400 psi, until the capillary tube is rinsed clean, which takes approximately 5 minutes. The capillary tube is then rinsed with methanol and dried under a flow of nitrogen. The capillary tube is then ready for filling with a new portion of the separation matrix. In this way, capillary tubes may be reused many times. Turn-around time between electrophoretic runs is currently approximately 15 minutes, but may be shortened with automation.

A CE instrument having an array of capillary tubes is typically used for processing of numerous nucleic acid samples. See Richard A. Mathies and Xiaohua C. Huang, "Capillary array electrophoresis: an approach to high-speed, high-throughput DNA sequencing," *Nature*, Vol. 359, Sep. 10, 1992, pages 167–169. For example, a 48 capillary tube array in an electrophoresis apparatus allows simultaneous filling of 48 capillary tubes with the separation matrix. This arrangement corresponds conveniently to half of a standard microtiter plate. The nucleic acid samples are then each introduced to an individual capillary tube at its entrance end. Then, the electrophoretic separations are simultaneously performed on all capillary tubes of the array having samples. Cleaning of the capillary tubes for further sample separations may also occur in all tubes simultaneously. This array system allows for high throughput of nucleic acid samples. The separation matrix of the present invention contributes significantly to the usage of such an apparatus since the matrix is easily replaceable, both because of its low viscosity which allows for rapid filling and cleaning of the capillary tubes, and because the separation matrix is inexpensive and convenient to use.

Because no polymerization is necessary with the separation matrix of the present invention, there is no delay between the time of filling the capillary tube with the matrix and the time of using the separation matrix for an electrophoretic run. The pre-run before introduction of the sample is a standard step in capillary electrophoresis systems having a variety of matrices, and is usually done to equilibrate the electrophoretic system and to standardize the electrophoretic runs of various samples. Electrophoresis is usually performed at room temperature for sequencing and sizing applications of nucleic acids.

FIG. 1 presents a plot of peak spacings and peak widths as a function of base number for an M13mp18 ddT sequencing reaction (1 μg DNA, 15 second injection at 12 kV, run at 12 kV), electrophoresed with the separation matrix of the present invention, shown in solid lines, and with a crosslinked polyacrylamide (3%T/3%C) of the prior art, shown in dotted lines. Line 10 represents peak spacing and line 20 represents peak width of the HEC/urea/formamide separation matrix. Line 15 and line 25 represent the peak spacing and peak width, respectively, of the prior art matrix. FIG. 1 illustrates the trend of both the present invention and the prior art matrix to provide an LOR of between 500 to 600 base pairs.

Figure 2:
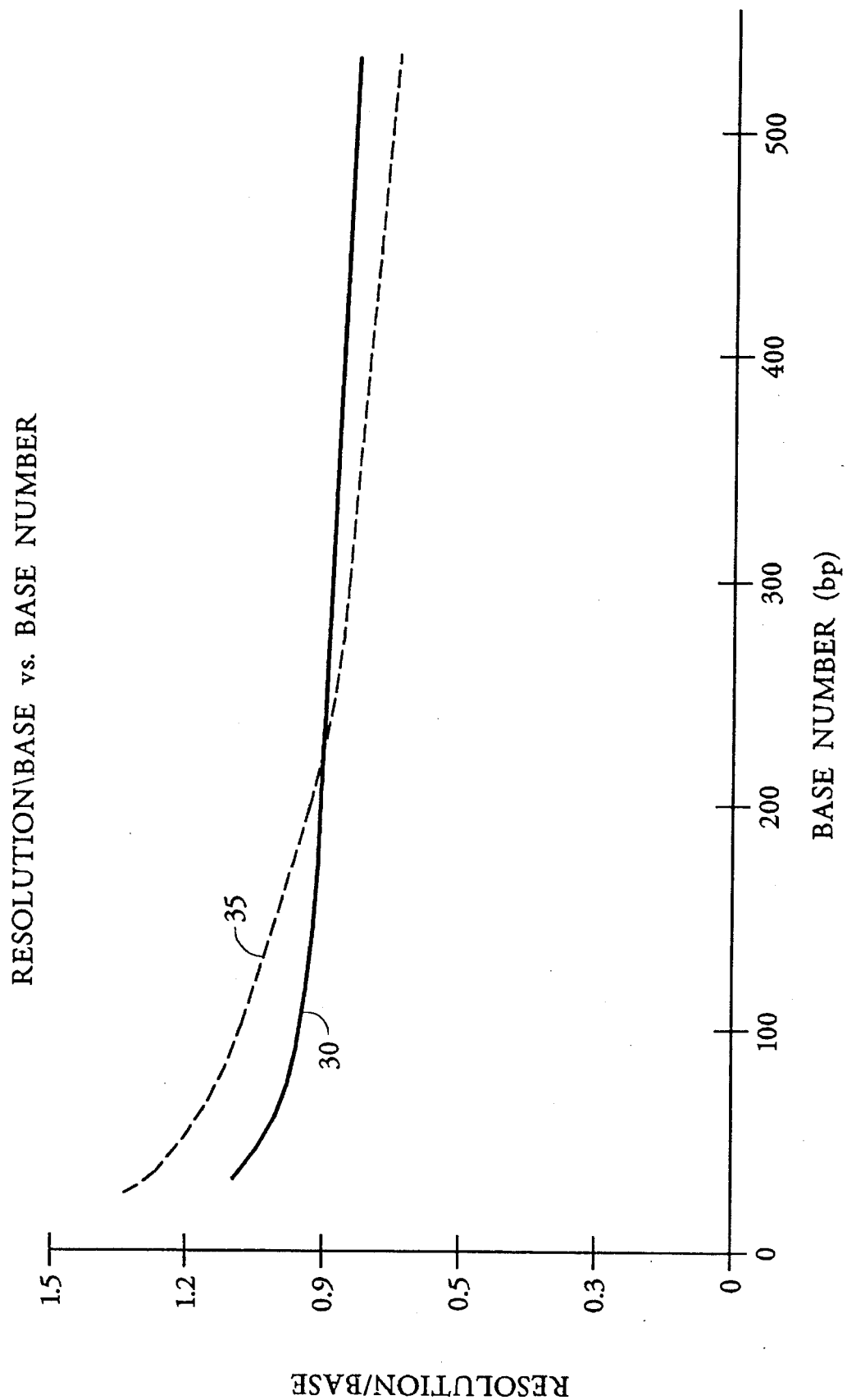
FIG. 2 is a graphical representation of resolution/base versus base number for the separation matrix of the present invention and a prior art separation matrix.

The resolution of the separation matrix of the present invention is comparable to that of polyacrylamide matrices, as well, as seen in FIG. 2. FIG. 2 presents the resolution per base versus base number, for the present invention, shown by solid line 30, and a crosslinked polyacrylamide matrix (3%T/3%C) of the prior art, shown by dotted line 35. The resolution is defined as taught in Paul D. Grossman, "Electrophoretic separation of DNA sequencing extension products using low-viscosity entangled polymer networks," *Journal of Chromatography A*, 663 (1994), pages 219–227.

The urea of the separation matrix is a powerful denaturant which causes nucleic acids to run through the capillary tube in single-stranded form. The samples which are loaded into the capillary tube are generally single-stranded, as in the case of DNA sequencing reaction mixtures, but may be in double-stranded form. The latter samples would become single-stranded during the electrophoretic run.

Although capillary electrophoresis of nucleic acids has been emphasized, the present invention may be applicable to other separations that are required to occur under denaturing conditions.

We claim:

1. A denaturing separation matrix for capillary electrophoresis of nucleic acids, the matrix comprising:

an aqueous solution of hydroxyethyl cellulose in combination with urea, the urea being present at a concentration in the range of 5M to 7M wherein the hydroxyethyl cellulose comprises 1 to 3% w/v of the solution.

2. The separation matrix of claim 1 wherein the hydroxyethyl cellulose comprises 2% w/v of the solution.

3. The separation matrix of claim 1 wherein the hydroxyethyl cellulose has a molecular weight range of 90,000 to 105,000 daltons.

4. The separation matrix of claim 1 wherein the hydroxyethyl cellulose is substantially free of charged impurities.

5. The separation matrix of claim 1 wherein the urea is present in the solution at a concentration of 6M.

6. The separation matrix of claim 1 wherein the solution further comprises formamide at a concentration of less than or equal to 30% v/v.

7. The separation matrix of claim 6 wherein the formamide comprises 10% v/v of the solution.

8. The separation matrix of claim 1 wherein the aqueous solution further comprises Tris-borate and EDTA (TBE).

9. The separation matrix of claim 8 wherein the TBE is at a concentration in the range of 0.5 x to 2 x.

10. The separation matrix of claim 1 wherein the aqueous solution further comprises 89 mM Tris-borate buffer, and 2 mM EDTA, at pH 8.0.

11. A separation matrix for capillary electrophoresis of nucleic acids, the matrix comprising:

2% w/v hydroxyethyl cellulose, and 5 to 7M urea, in a solution of 1 x TBE.

12. The separation matrix of claim 11 wherein the urea is present in the separation matrix at a concentration of 6M.

13. The separation matrix of claim 11 further comprising less than or equal to 30% v/v formamide.

14. The separation matrix of claim 13 wherein the formamide is present at a concentration of 10% v/v.

15. The separation matrix of claim 11 wherein the hydroxyethyl cellulose is substantially free of charged impurities.

16. A method of making a denaturing separation matrix for capillary electrophoresis comprising:

dissolving hydroxyethyl cellulose and urea in water to produce a solution having a concentration of at least 2% w/v of the hydroxyethyl cellulose and a concentration of at least 6M of the urea, purifying the hydroxyethyl cellulose and urea solution by contact with an ion-exchange resin, separating the purified hydroxyethyl cellulose and urea solution from the resin, adding Tris-borate and EDTA (TBE) to a portion of the purified hydroxyethyl cellulose and urea solution and diluting the solution, if necessary, to produce a separation matrix having a final concentration of 2% w/v hydroxyethyl cellulose, 6M urea, and 1 x TBE.

17. The method of claim 16 further comprising:

adding formamide to the portion of the purified hydroxyethyl cellulose and urea solution to provide a concentration of 10% v/v formamide in the separation matrix.

18. The method of claim 16 further comprising:

adding formamide to the hydroxyethyl cellulose and urea solution before the hydroxyethyl cellulose and urea solution is purified to provide a concentration of at least 10% v/v formamide in the hydroxyethyl cellulose and urea solution and a final concentration in the separation matrix of 10% v/v formamide.

19. The method of claim 16 further comprising:

degassing of the separation matrix prior to use.

20. The method of claim 16 further comprising:

centrifuging the separation matrix, and removing a portion of the resulting supernatant for use.

* * * * *